(12) United States Patent
Tahara

(10) Patent No.: US 11,561,162 B2
(45) Date of Patent: Jan. 24, 2023

(54) INFORMATION PROCESSING DEVICE, INFORMATION PROCESSING SYSTEM, AND INFORMATION PROCESSING METHOD

(71) Applicant: SONY CORPORATION, Tokyo (JP)

(72) Inventor: Katsutoshi Tahara, Tokyo (JP)

(73) Assignee: SONY CORPORATION, Tokyo (JP)

( * ) Notice: Subject to any disclaimer, the term of this patent is extended or adjusted under 35 U.S.C. 154(b) by 142 days.

(21) Appl. No.: 16/979,691

(22) PCT Filed: Jan. 28, 2019

(86) PCT No.: PCT/JP2019/002718
§ 371 (c)(1),
(2) Date: Sep. 10, 2020

(87) PCT Pub. No.: WO2019/181205
PCT Pub. Date: Sep. 26, 2019

(65) Prior Publication Data
US 2021/0041342 A1    Feb. 11, 2021

(30) Foreign Application Priority Data

Mar. 19, 2018    (JP) .............................. JP2018-051001

(51) Int. Cl.
*G01N 15/14*    (2006.01)
*G01N 21/53*    (2006.01)
(Continued)

(52) U.S. Cl.
CPC ......... *G01N 15/1429* (2013.01); *G01N 21/53* (2013.01); *G01N 21/6402* (2013.01);
(Continued)

(58) Field of Classification Search
CPC .... G01N 15/1429; G01N 15/14; G01N 21/53; G01N 21/6486; G01N 21/6402;
(Continued)

(56) References Cited

U.S. PATENT DOCUMENTS

| 2005/0112541 A1* | 5/2005 | Durack | ................. G01N 33/48 |
| | | | 435/40.5 |
| 2009/0108214 A1 | 4/2009 | Shinoda et al. | |

(Continued)

FOREIGN PATENT DOCUMENTS

| CN | 101419171 A | 4/2009 |
| CN | 103890564 A | 6/2014 |

(Continued)

OTHER PUBLICATIONS

International Search Report and Written Opinion of PCT Application No. PCT/JP2019/002718, dated Mar. 19, 2019, 08 pages of ISRWO.

*Primary Examiner* — Hoa Q Pham
(74) *Attorney, Agent, or Firm* — Chip Law Group

(57) ABSTRACT

It is aimed to provide a technology that enables highly accurate device performance evaluation and device adjustment in optical analysis of microparticles, using the same type of beads. The present technology provides an information processing device including an information processing unit that acquires a plurality of fluorescence intensities at a plurality of light irradiation powers for a fluorescence signal from a sample including particles labeled with a fluorescent dye having a single fluorescence intensity, recognizes an intensity range of each of the plurality of fluorescence intensities detected on the basis of a fluorescence intensity balance of the sample, and calculates information relating to sensitivity of a fluorescence detection unit.

10 Claims, 5 Drawing Sheets

(51) Int. Cl.
  *G01N 21/64*   (2006.01)
  *G01N 33/58*   (2006.01)
(52) U.S. Cl.
  CPC ....... *G01N 21/6486* (2013.01); *G01N 33/582* (2013.01); *G01N 2015/149* (2013.01)
(58) Field of Classification Search
  CPC .. G01N 21/6428; G01N 21/64; G01N 21/274; G01N 33/582; G01N 33/54346; G01N 2015/149; G01N 2015/1452; G01N 2021/6439
  USPC ........................... 356/335–343, 73, 300–326
  See application file for complete search history.

(56) References Cited

U.S. PATENT DOCUMENTS

2014/0370509 A1    12/2014  Wild et al.
2019/0309364 A1*   10/2019  Evans ................ G01N 15/1459

FOREIGN PATENT DOCUMENTS

| EP | 2053381 A2 | 4/2009 |
| EP | 2584342 A1 | 4/2013 |
| JP | 04-109141 A | 4/1992 |
| JP | 2003-083894 A | 3/2003 |
| JP | WO 2006/088047 A1 * | 8/2006 |
| JP | 2009-109218 A | 5/2009 |
| JP | 2014-534430 A | 12/2014 |
| JP | 2016-217789 A | 12/2016 |
| KR | 10-2009-0042713 A | 4/2009 |
| WO | 2016/185755 A1 | 11/2016 |

* cited by examiner

INFORMATION PROCESSING DEVICE, INFORMATION PROCESSING SYSTEM, AND INFORMATION PROCESSING METHOD

CROSS REFERENCE TO RELATED APPLICATIONS

This application is a U.S. National Phase of International Patent Application No. PCT/JP2019/002718 filed on Jan. 28, 2019, which claims priority benefit of Japanese Patent Application No. JP 2018-051001 filed in the Japan Patent Office on Mar. 19, 2018. Each of the above-referenced applications is hereby incorporated herein by reference in its entirety.

TECHNICAL FIELD

The present technology relates to an information processing device that processes fluorescence information obtained from a fluorescence-labeled sample. In more detail, the present technology relates to an information processing device, an information processing system, and an information processing method that obtain information relating to the sensitivity in fluorescence detection on the basis of fluorescence information obtained from a fluorescence-labeled sample.

BACKGROUND ART

In recent years, with the development of examination techniques, techniques are being devised in which biological microparticles such as cells and microorganisms, microparticles such as microbeads, or the like are allowed to flow through a flow path, and the microparticles are individually measured or measured microparticles are analyzed or sorted during the step of flowing.

As a typical example of such techniques of analyzing or sorting microparticles, technological improvements in an examination technique called flow cytometry is rapidly progressing. The flow cytometry is an examination technique for detecting the fluorescence or scattered light emitted from each microparticle by releasing microparticles to be analyzed into a fluid in an aligned state and irradiating the microparticles with a laser beam or the like, to analyze or sort the microparticles.

In the analysis of microparticles represented by the flow cytometry or the like, an optical technique is often used in which the microparticles to be analyzed are irradiated with light such as a laser and the fluorescence or scattered light emitted from the microparticles is detected. Then, a histogram is extracted by analysis computer and software and analysis is performed by utilizing the detected optical information.

In the optical analysis of microparticles, prior to the optical measurement actually performed on microparticles to be inspected, quality control (QC) is sometimes performed to verify the accuracy or the like of the measurement, or confirm the operation of the device and standardize the device, for example. In this quality control, in a case where the device performance is evaluated, usually, for example, a plurality of types of beads (3-peak beads, 6-peak beads, 8-peak beads, and the like) labeled with fluorescent dyes having different fluorescence intensities is used.

When a measurement is performed between a plurality of fluorescent dyes, as a technology of performing fluorescence correction, for example, Patent Document 1 discloses a technology achieved by devising a program intended to calculate the centroid value of a fluorescent population regarding fluorescence-labeled test cells obtained by a flow cytometer, from a two-dimensional correlation diagram of the fluorescence-labeled test cells, and perform the correction computation for the fluorescence values of the fluorescence-labeled test cells relevant to the centroid value, using a predetermined determinant and the fluorescence values, so as to be capable of performing fluorescence correction when measuring fluorescence using a plurality of laser beams as well as between a plurality of fluorescent dyes, and also capable of carrying out fluorescence correction without re-preparing the test object even after a measurement process for test cells is finished.

Meanwhile, in the quality control, in a case where the device is adjusted, usually, for example, one type of beads labeled with a fluorescent dye having a single fluorescence intensity capable of obtaining a wide spectrum (align-check beads, Ultra Rainbow fluorescent particles, and the like) is used.

CITATION LIST

Patent Document

Patent Document 1: Japanese Patent Application Laid-Open No. 2003-83894

SUMMARY OF THE INVENTION

Problems to be Solved by the Invention

As described above, in the quality control in the optical analysis of microparticles, beads suitable for evaluating the device performance and beads suitable for adjusting the device are different from each other, and it has been thus necessary to secure two types of beads, namely, the beads for evaluating the device performance and the beads for adjusting the device.

Furthermore, beads including a plurality of kinds labeled with fluorescent dyes having different fluorescence intensities, such as 3-peak beads, 6-peak beads, and 8-peak beads suitable for evaluating the device performance have a narrow excitation wavelength region or fluorescence wavelength region, and have had such a disadvantage that the obtained fluorescence intensity is generally low, and the obtained intensity is extremely lowered particularly at 700 nm or less.

Moreover, although non-fluorescent beads have been used for measuring the background of the device, it has been impossible to reflect 100% of the state of the device because actually a small amount of fluorescence is obtained.

Additionally, automatic separation of beads including a plurality of kinds labeled with fluorescent dyes having different fluorescence intensities, such as 3-peak beads, 6-peak beads, and 8-peak beads, requires an advanced technology, and it has been very difficult to separate between fluorescence peaks obtained from respective types of beads when the fluorescence peaks are adjacent to each other.

In view of this, a main object of the present technology is to provide a technology that enables highly accurate device performance evaluation and device adjustment in optical analysis of microparticles using the same type of beads.

Solutions to Problems

As a result of earnest research to accomplish the above-mentioned object, the inventors of the present application have focused on the setting of the light irradiation power and succeeded in highly accurately evaluating the device performance as well, using a single type of beads labeled with a fluorescent dye having a single fluorescence intensity by which a wide spectrum is obtained, which has been used in the case of adjusting the device in the conventional quality control, to finally complete the present technology.

That is, first, the present technology provides an information processing device including an information processing unit that acquires a plurality of fluorescence intensities at a plurality of light irradiation powers for a fluorescence signal from a sample including particles labeled with a fluorescent dye having a single fluorescence intensity, recognizes an intensity range of each of the plurality of fluorescence intensities detected on the basis of a fluorescence intensity balance of the sample, and calculates information relating to sensitivity of a fluorescence detection unit.

In the present technology, the light irradiation powers can adopt at least three or more, or at least five or more different powers.

In the present technology, the information processing unit can also recognize a fluorescence intensity range obtained from a sheath liquid that does not contain the sample, as a minimum intensity range, and calculate the information relating to the sensitivity of the fluorescence detection unit.

The information relating to the sensitivity of the fluorescence detection unit that can be calculated by the information processing device according to the present technology includes a degree of linearity between the fluorescence intensities and a number of particles and/or fluorescence detection sensitivity.

In the present technology, a trigger can be activated at a constant light irradiation power by an excitation laser different from an excitation laser for acquiring the plurality of fluorescence intensities at the plurality of light irradiation powers.

In the present technology, the information processing unit can also calculate information relating to adjustment of the fluorescence detection unit on the basis of the fluorescence signal from the sample including the particles labeled with the fluorescent dye having the single fluorescence intensity.

Next, the present technology provides an information processing system including:
an irradiation unit that irradiates a sample including particles labeled with a fluorescent dye having a single fluorescence intensity with light;
a detection unit that detects a fluorescence signal from the sample; and
an information processing unit that acquires a plurality of fluorescence intensities at a plurality of light irradiation powers for the fluorescence signal, recognizes an intensity range of each of the plurality of fluorescence intensities detected on the basis of a fluorescence intensity balance of the sample, and calculates information relating to sensitivity of the detection unit.

The present technology further provides an information processing method that performs an information processing step of acquiring a plurality of fluorescence intensities at a plurality of light irradiation powers for a fluorescence signal from a sample including particles labeled with a fluorescent dye having a single fluorescence intensity, recognizing an intensity range of each of the plurality of fluorescence intensities detected on the basis of a fluorescence intensity balance of the sample, and calculating information relating to sensitivity of a fluorescence detection unit.

Effects of the Invention

According to the present technology, highly accurate device performance evaluation and device adjustment in optical analysis of microparticles is enabled using the same type of beads.

Note that the effects described herein are not necessarily limited and any effects described in the present technology may be applied.

MODE FOR CARRYING OUT THE INVENTION

Hereinafter, preferred modes for carrying out the present technology will be described with reference to the drawings. Embodiments described below indicate examples of representative embodiments of the present technology, and the scope of the present technology is not narrowly interpreted by these embodiments. Note that the description will be given in the following order.

1. Information Processing Device 1
(1) Information Processing Unit 11
2. Information Processing System 10
(1) Information Processing Unit 11
(2) Light Irradiation Unit 12
(3) Fluorescence Detection Unit 13
(4) Sorting Unit 14
3. Information Processing Method <1. Information Processing Device 1>

Figure 1:
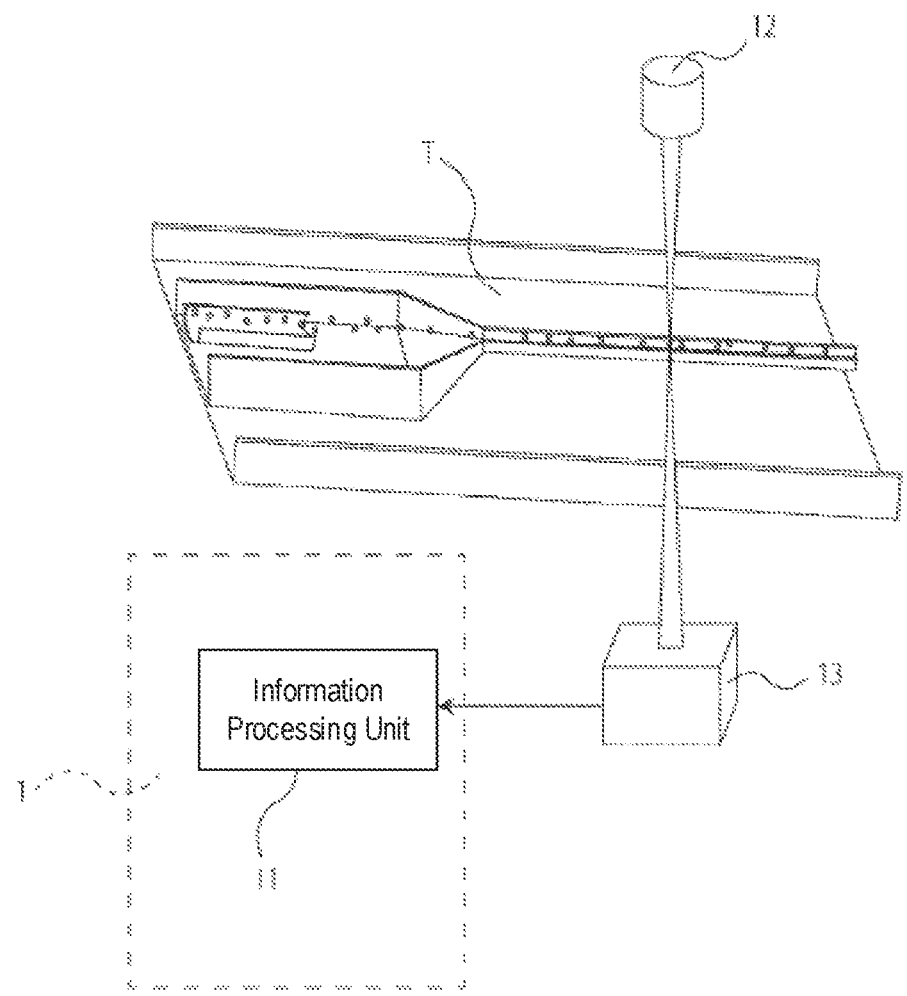
FIG. 1 is a schematic conceptual diagram schematically illustrating an example of a flow cytometer capable of using an information processing device 1 according to the present technology.

An information processing device 1 according to the present technology is an information processing device that can be used when performing optical analysis of microparticles, and includes at least an information processing unit 11. A flow cytometer is cited as an example of a device for performing optical analysis of microparticles capable of using the information processing device 1 according to the present technology. FIG. 1 is a schematic conceptual diagram schematically illustrating an example of the flow cytometer capable of using the information processing device 1 according to the present technology.

In the flow cytometer capable of using the information processing device 1 according to the present technology, by detecting optical information obtained from microparticles aligned in a row in a flow cell (flow path P), analysis and sorting of the microparticles can be performed.

The flow cytometer may include the flow path P in advance, but it is also possible to install a commercially available flow path P or a disposable chip provided with the flow path P or the like in the flow cytometer to perform analysis or sorting.

Figure 6:
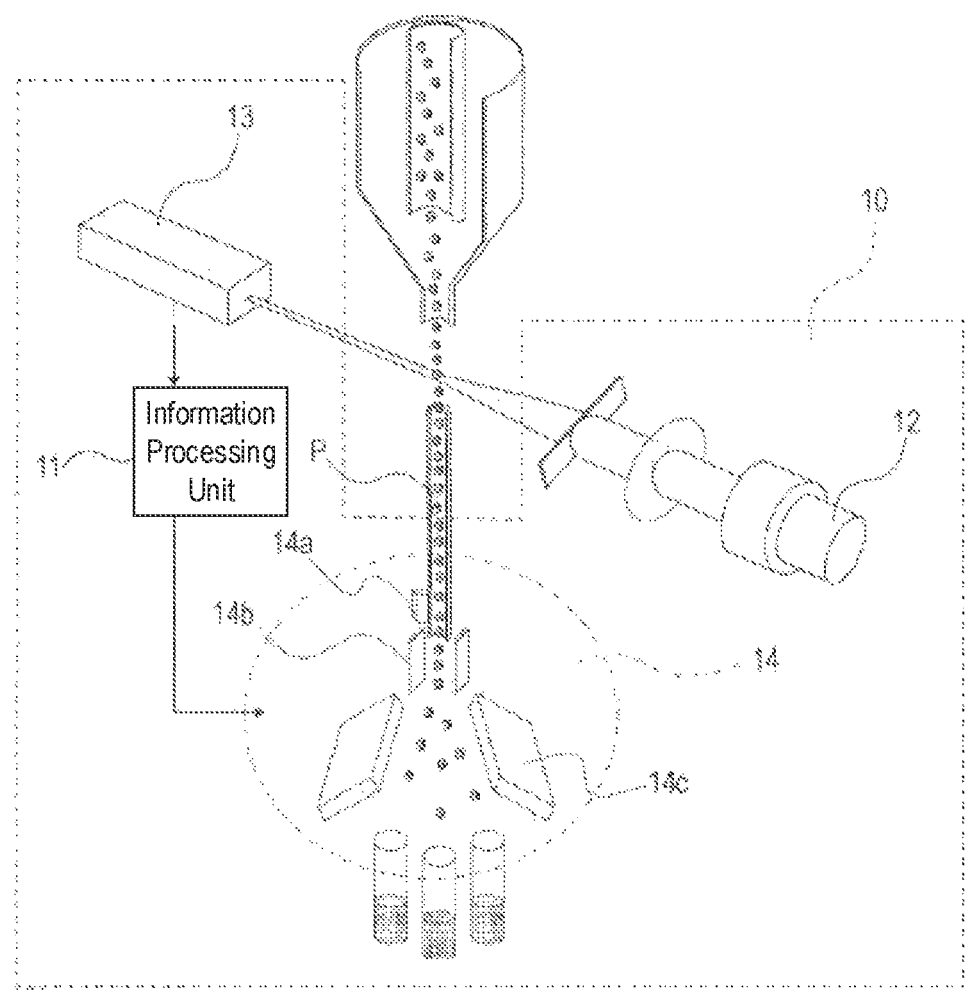
FIG. 6 is a schematic conceptual diagram schematically illustrating an example of a flow cytometer capable of using an information processing system 10 according to the present technology.

The mode of the flow path P is not particularly limited and can be freely designed. For example, the mode of the flow path P is not restricted to a flow path P formed in a two-dimensional or three-dimensional substrate T constituted by plastic or glass or the like, as illustrated in FIG. 1, and the flow path P such as one used in a conventional flow cytometer as illustrated in FIG. 6 described later can also be used for the flow cytometer.

Furthermore, the flow path width, flow path depth, and flow path cross-sectional shape of the flow path P are also not particularly limited as long as the mode capable of forming a laminar flow is achieved, and can be freely designed. For example, a micro flow path having a flow path width of 1 mm or less can also be used for the flow cytometer. In particular, a micro flow path having a flow path width of about 10 μm or more and about 1 mm or less can be preferably used by a flow cytometer capable of using the information processing device 1 according to the present technology.

(1) Information Processing Unit 11

The information processing unit 11 calculates information relating to the sensitivity of a fluorescence detection unit (hereinafter, also referred to as "sensitivity information"). The sensitivity information is calculated in the following procedure.

[Acquisition of Fluorescence Intensity]

First, a plurality of fluorescence intensities at a plurality of light irradiation powers is acquired for a fluorescence signal from a sample including particles labeled with a fluorescent dye having a single fluorescence intensity. For example, a fluorescence signal obtained by converting optical information detected in a fluorescence detection unit 13 of the flow cytometer described later into an electrical signal (voltage pulse), and performing analog-digital conversion on the converted electrical signal can be used for the fluorescence signal.

Examples of the sample including particles labeled with a fluorescent dye having a single fluorescence intensity include align-check beads, Ultra Rainbow fluorescent particles, and the like.

Furthermore, as the sample usable in the present technology, a sample containing particles labeled with one type of fluorescent dye can also be used. In this case, as the fluorescent dye usable in the present technology, for example, Cascade Blue, Pacific Blue, Fluorescein isothiocyanate (FITC), Phycoerythrin (PE), Propidium iodide (PI), Texas red (TR), Peridinin chlorophyll protein (PerCP), Allophycocyanin (APC), 4',6-Diamidino-2-phenylindole (DAPI), Cy3, Cy5, Cy7, Brilliant Violet (BV421), and the like can be used.

As the plurality of light irradiation powers, it is favorable to use three or more different powers, more favorable to use five or more different powers, and even more favorable to use eight or more different powers. By using three or more different powers, the degree of linearity (Linearity) between the fluorescence intensities and the number of particles and the fluorescence detection sensitivity (molecules of equivalent soluble fluorochromes (MESF)) can be worked out as the information relating to the sensitivity of the fluorescence detection unit, and by using five or more different powers, a Q value and a B value can be further worked out, such that the device performance can be evaluated with higher accuracy.

[Recognition of Intensity Range]

Figure 2:
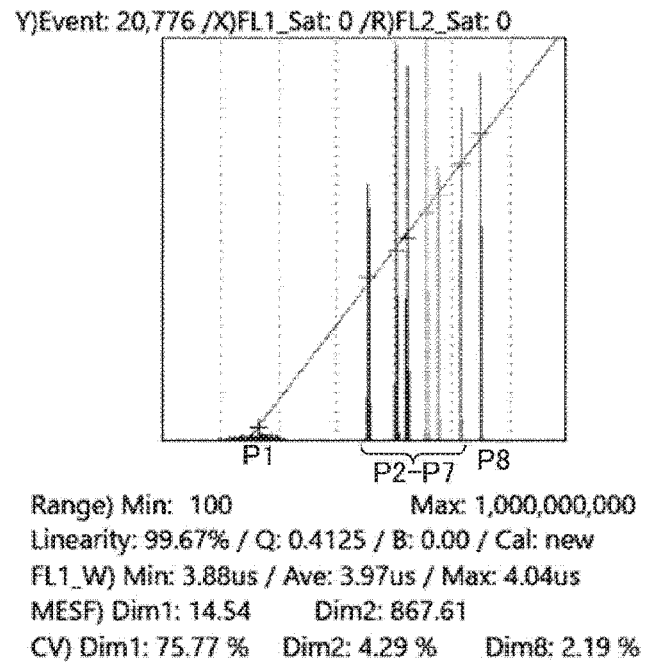
FIG. 2 is a drawing-substitute graph illustrating an example of the result of recognizing respective intensity ranges at eight types of light irradiation powers in the fluorescence region of Brilliant Violet (BV421) using Ultra Rainbow fluorescent particles.
Figure 3:
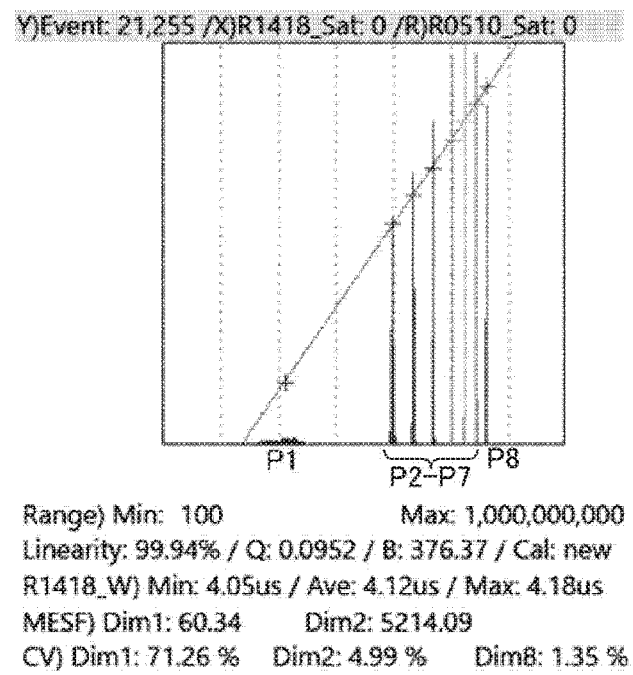
FIG. 3 is a drawing-substitute graph illustrating an example of the result of recognizing respective intensity ranges at eight types of light irradiation powers in the fluorescence region of Phycoerythrin (PE) using Ultra Rainbow fluorescent particles.

Next, the intensity range of each of the acquired fluorescence intensities is recognized on the basis of the fluorescence intensity balance of the sample. For example, in a case where the device performance is evaluated using eight types of light irradiation powers, each of eight types of intensity ranges at each light irradiation power is recognized. Examples of the results of recognizing each of the eight types of intensity ranges are illustrated in FIGS. 2 and 3. FIG. 2 depicts a result obtained from a sample using Brilliant Violet (BV421) as an example of the fluorescent dye, and FIG. 3 depicts a result obtained from a sample using Phycoerythrin (PE) as an example of the fluorescent dye. In each figure, the horizontal axis denotes the fluorescence intensity, and the vertical axis denotes the number of particles (this similarly applies hereinafter).

Specifically, while the light irradiation power is being changed, fluorescence obtained from a sample including particles labeled with a fluorescent dye having a single fluorescence intensity is adapted to a desired level, and data of the maximum peak in a specified number of events at a light irradiation power fixed to the value at the desired level is acquired (see reference signs P8 in FIGS. 2 and 3). Next, similarly, the light irradiation power is changed to acquire the data of six peaks at the desired level (see reference signs P2 to P7 in FIGS. 2 and 3). Finally, the median value of the widths of the obtained seven pieces of peak data (data of the maximum peak and six peaks) is worked out, and the light irradiation power is set to a power at the time of measurement; then, data for only a sheath liquid, which does not contain the above data of the sample, is acquired at intervals of the worked-out median value of the widths (see reference signs P1 in FIGS. 2 and 3). With such a procedure, each of the eight types of intensity ranges obtained from the above-mentioned sample is recognized while the light irradiation power is being changed.

In the conventional evaluation of the device performance, usually, for example, a plurality of types of beads (3-peak beads, 6-peak beads, 8-peak beads, and the like) labeled with fluorescent dyes having different fluorescence intensities has been used, and it has been thus necessary to separate between a plurality of fluorescence intensity populations on the basis of a plurality of detected fluorescence intensities. An advanced technology is required for the separation between the fluorescence intensity populations, and for example, labor such as repeated clustering has been vitally needed.

On the other hand, in the present technology, the light irradiation power is changed to recognize each intensity range, which allows respective intensity ranges to be recognized in a preliminarily divided state into a plurality of parts. Therefore, it is not necessary to separate between the respective intensity populations. Furthermore, as mentioned earlier, there has been a disadvantage that an advanced technology is required for separating between the fluorescence intensity populations and the misrecognition of each population occurs; in the present technology, however, such misrecognition cannot be caused. As a result, the device performance can be evaluated more easily with higher accuracy.

In addition, in the conventional evaluation of the device performance, non-fluorescent beads have been used for measuring the background of the device, but it has been impossible to reflect 100% of the state of the device because actually a small amount of fluorescence is obtained.

On the other hand, in the present technology, as described above, at the time of acquiring the fewest peak (see reference signs P1 in FIGS. 2 and 3), a background signal of the device is acquired while the light irradiation power is emitted at a power at the time of measurement, and therefore the exact state of the device can be evaluated. In particular, optical noise and electrical noise are often dominant to the background, and in the optical noise, the autofluorescence component from the sheath liquid is also included. In a case where these types of noise are larger, the fluorescence detection sensitivity (MESF) becomes higher.

In the present technology, it is favorable to provide different excitation lasers for an excitation laser used for a channel to be evaluated and an excitation laser for a channel to activate a trigger. This is because a trigger can be activated stably at a constant light irradiation power by using a laser different from an excitation laser for acquiring a plurality of fluorescence intensities at a plurality of light irradiation powers. At this time, in the case of spatially-separated positioning, it is favorable to pick out a channel from which a signal having a good signal-to-noise (S/N) ratio can be obtained, for a trigger from scattered light or fluorescence. Furthermore, in the case of co-linear positioning, it is favorable to pick out a channel in which the level difference obtained between lasers is large and the output on the side of activating a trigger is large.

[Calculation of Sensitivity Information]

The information relating to the sensitivity of the fluorescence detection unit is calculated on the basis of the intensity range of each of the plurality of fluorescence intensities recognized above. The information relating to the sensitivity of the fluorescence detection unit that can be calculated by the information processing device 1 according to the present technology includes the degree of linearity (Linearity) between the fluorescence intensities and the number of particles, the fluorescence detection sensitivity (molecules of equivalent soluble fluorochromes (MESF)), the Q value, B value, and the like. Hereinafter, a description will be given of an example of a method of calculating each piece of sensitivity information in a case where the device performance is evaluated using eight types of light irradiation powers.

(a) Definition
Dim1: Minimum Peak
Dim2: Second Minimum Peak
Dim3: Third Minimum Peak
•
•
•
Dim8: Maximum Peak
MFI: Mean Fluorescence Intensity (a value obtained by transforming the highest and lowest values in the average fluorescence signal intensity into 1 and 0)
ME2 to ME8: Reference MESF Values for Dim2 to Dim8
MESF: Molecules of Equivalent Soluble Fluorochromes (the number of fluorescent molecules per particle)
Average Values of Dim1 to Dim8: MFI1 to MFI8
Log Values of MFI1 to MFI8: Log MFI1 to Log MFI8
Reference Values for Dim1 to Dim8: ME1 to ME8
Log Values of ME2 to ME8: Log ME2 to Log ME8
Computed MESF Value of Dim1: MESF (b) Degree of Linearity (Linearity)
A correlation coefficient (R) is worked out using Log MFI2 to Log MFI8 and Log ME2 to Log ME8, and is taken as the degree of linearity (Linearity). The closer the degree of linearity is to 100%, the better.

Figure 4:
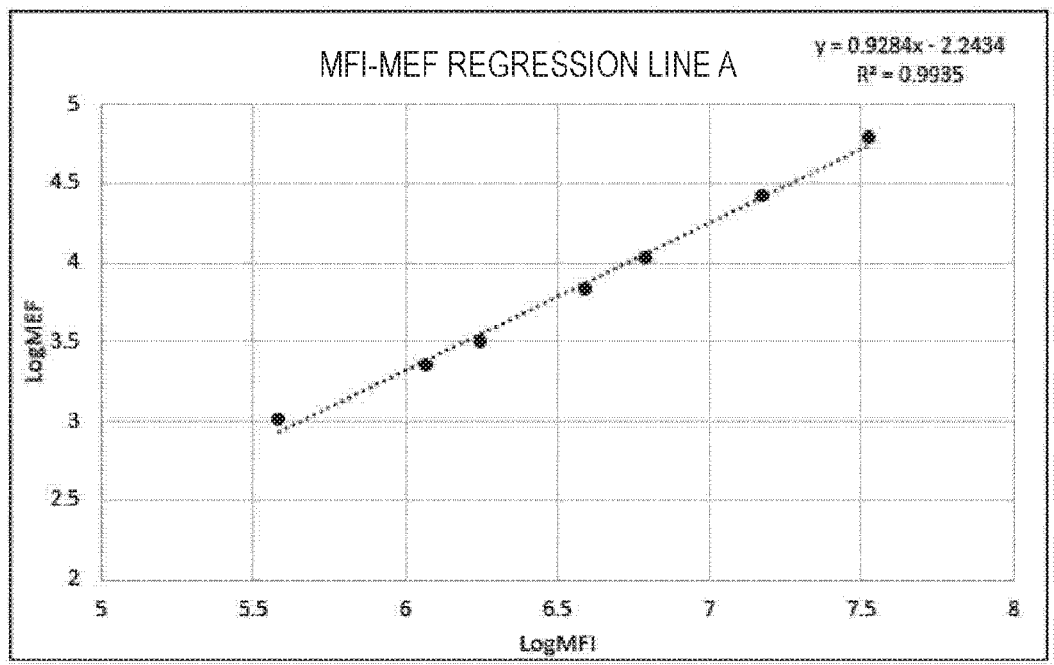
FIG. 4 is a drawing-substitute graph illustrating an example of a regression line A in the case of evaluating the device performance using eight types of light irradiation powers.

(c) Fluorescence Detection Sensitivity (Molecules of Equivalent Soluble Fluorochromes (MESF))
[1] A regression line A is worked out using Log MFI2 to Log MFI8 and Log ME2 to Log ME8, and the slope of the line is taken as a and the intercept of the line is taken as b. FIG. 4 illustrates an example of the regression line A in the case of evaluating the device performance using eight types of light irradiation powers.
[2] The fluorescence detection sensitivity (MESF) is worked out using following mathematical formula (1).

[Mathematical Formula 1]

$$MESF = 10^{(a \times Log\ MFI1 + b)} \quad (1)$$

The closer the fluorescence detection sensitivity (MESF) is to the reference value of Dim1 (normally, 0), the better.

Figure 5:
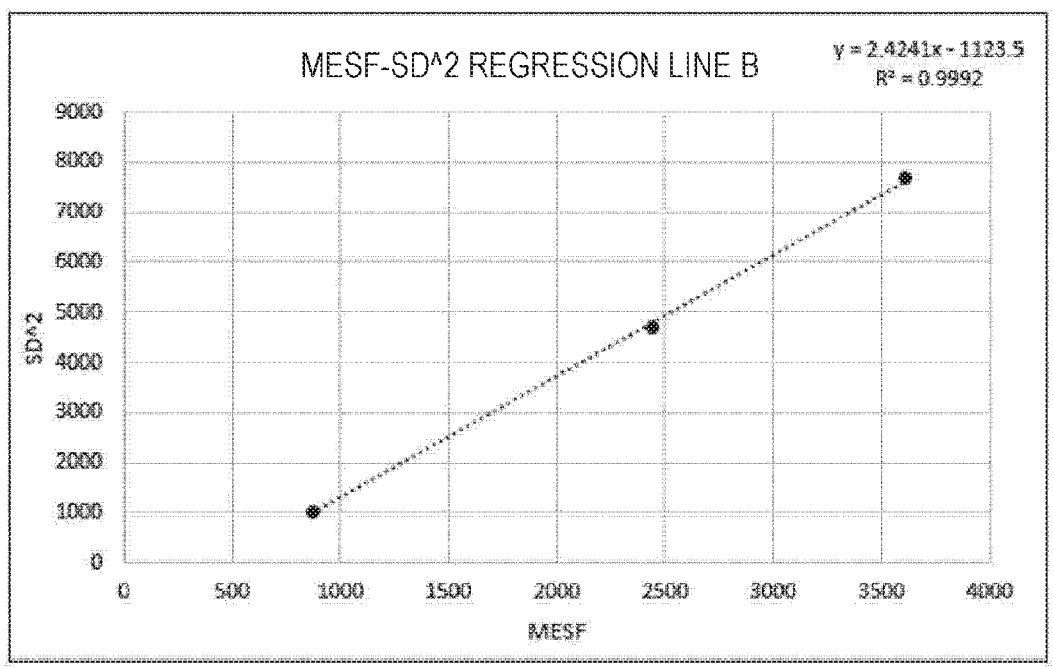
FIG. 5 is a drawing-substitute graph illustrating an example of a regression line B in the case of evaluating the device performance using eight types of light irradiation powers.

(d) Q Value and B Value
[1] The square of a standard deviation SD of the fluorescence detection sensitivities (MESF) of Dim2 to Dim8 is worked out.
[2] With the fluorescence detection sensitivity (MESF) as an x-axis and the square of the standard deviation SD as a y-axis, a regression line B is worked out at any peak, and the slope of the line is taken as a and the intercept of the line is taken as b. FIG. 5 illustrates an example of the regression line B in the case of evaluating the device performance using eight types of light irradiation powers.
[3] The Q value and B value are worked out using following mathematical formulas (2) and (3).

[Mathematical Formula 2]

$$Q\ \text{Value} = 1/a \quad (2)$$

[Mathematical Formula 3]

$$B\ \text{Value} = b/a \quad (3)$$

[Calculation of Adjustment Information]

In the present technology, since the device performance is evaluated using one type of sample labeled with a fluorescent dye having a single fluorescence intensity, which has been often used in the past in a case where the device is adjusted, the device can also be adjusted using the same sample. That is, in the present technology, the information processing unit can also calculate information relating to the adjustment of the fluorescence detection unit on the basis of a fluorescence signal from a sample including particles labeled with a fluorescent dye having a single fluorescence intensity. Note that, as a specific method of adjusting the device, one or two or more known methods can be freely selected and used.

<2. Information Processing System 10>

An information processing system 10 according to the present technology is an information processing system that can be used when performing optical analysis of microparticles, and includes at least an information processing unit 11, a light irradiation unit 12, and a fluorescence detection unit 13. Furthermore, a sorting unit 14 and the like can also be included, if necessary. A flow cytometer is cited as an example of a device for performing optical analysis of microparticles capable of using the information processing system 10 according to the present technology. FIG. 6 is a schematic conceptual diagram schematically illustrating an example of a flow cytometer capable of using the information processing system 10 according to the present technology.

(1) Information Processing Unit 11

In the information processing unit 11, a plurality of fluorescence intensities at a plurality of light irradiation powers is acquired on the basis of a fluorescence signal acquired by the fluorescence detection unit described later, the intensity range of each of the plurality of fluorescence intensities detected on the basis of a fluorescence intensity balance of the sample is recognized, and information relating to the sensitivity of the detection unit is calculated. Since the details are the same as those of the information processing unit 11 of the information processing device 1 described above, the description thereof will be omitted here.

(2) Light Irradiation Unit 12

In the light irradiation unit 12, a sample including a plurality of particles labeled with fluorescent dyes having different fluorescence intensities is irradiated with light. The type of light for irradiation by the light irradiation unit 12 is not particularly limited, but in order to reliably generate fluorescence or scattered light from the particles, light having constant light direction, wavelength, and light intensity is desirable. A laser, a light emitting diode (LED), and the like can be cited as an example. In a case where a laser is used, the type of the laser is also not particularly limited; one or two or more lasers can be freely combined and used from among an argon ion (Ar) laser, a helium-neon (He—Ne) laser, a dye laser, a krypton (Cr) laser, a semiconductor laser, a solid-state laser combining a semiconductor laser and a wavelength conversion optical element, and the like.

(3) Fluorescence Detection Unit 13

In the fluorescence detection unit 13, a fluorescence signal from the sample is detected. The type of the fluorescence detection unit 13 that can be used in the present technology is not particularly limited as long as the fluorescence detection unit 13 can detect a fluorescence signal from a sample, and a known photodetector can be freely selected and adopted. For example, one or two or more pieces of equipment can be freely combined and adopted from among a fluorescence measuring instrument, a scattered light measuring instrument, a transmitted light measuring instrument, a reflected light measuring instrument, a diffracted light measuring instrument, an ultraviolet spectroscopic measuring instrument, an infrared spectroscopic measuring instrument, a Raman spectroscopic measuring instrument, a fluorescence resonance energy transfer (FRET) measuring instrument, a fluorescence in situ hybridization (FISH) measuring instrument, and other various spectrum measuring instruments; a photomultiplier tube (PMT) array or photodiode array in which light receiving elements such as PMTs or photodiodes are arranged one-dimensionally; a piece of equipment in which a plurality of independent detection channels such as charge coupled devices (CCDs) or complementary metal oxide semiconductors (CMOSs) or other two-dimensional light receiving elements is placed in order; and the like.

Furthermore, the installation location of the fluorescence detection unit 13 in the information processing system 10 according to the present technology is not particularly limited as long as the fluorescence signal from the sample can be detected, and can be freely designed. For example, as illustrated in FIGS. 1 and 6, it is favorable to dispose the fluorescence detection unit 13 on an opposite side of the light irradiation unit 12 with the flow path P interposed therebetween. This is because, by disposing the fluorescence detection unit 13 on an opposite side of the light irradiation unit 12 with the flow path P interposed therebetween, the light irradiation unit 12 and the fluorescence detection unit 13 can be disposed in a more free configuration. In addition, for example, since fluorescence is also radiated in a direction different from an incident direction of irradiation light, the fluorescence detection unit 13 is also allowed to be disposed on the same side as the light irradiation unit 12 or on a lateral end side of the light irradiation unit 12 by 90 degrees with respect to the flow path P.

(4) Sorting Unit 14

In the sorting unit 14, the particles are sorted on the basis of the fluorescence signal detected by the fluorescence detection unit 13 or the analysis result for the particles analyzed by the information processing unit 11. For example, the sorting unit 14 can sort the particles at a downstream point of the flow path P on the basis of the analysis results for the size, morphology, internal structure, and the like of the particles analyzed from the optical information.

More specifically, as illustrated in FIG. 6, for example, using a vibrating element 14*a* or the like that vibrates at a predetermined vibration frequency, the entire or a part of the flow path P is vibrated to generate a droplet from a discharge port of the flow path P. Note that, in this case, the vibrating element 14*a* to be used is not particularly limited, and a known vibrating element can be freely selected and used. A piezoelectric vibrating element or the like can be cited as an example. Furthermore, by adjusting the amount of liquid fed to the flow path P, the diameter of the discharge port, the vibration frequency of the vibrating element, and the like, the size of the droplet can be adjusted and droplets each containing a definite amount of test object can be generated.

Next, the generated droplets are charged with positive or negative charges on the basis of the analysis results for the size, morphology, internal structure, and the like of the analyzed particle (see reference sign 14*b* in FIG. 6). Then, the course of the charged droplets is altered to a desired direction by a counter electrode 14*c* to which a voltage is applied, and the droplets are sorted.

<3. Information Processing Method>

An information processing method according to the present technology is an information processing method that can be used when performing optical analysis of microparticles, and is a method that performs at least an information processing step. The specific information processing method performed in the information processing step is the same as the method performed by the information processing unit 11 of the information processing device 1 described above. Hereinafter, an example of the flow of an information process using the information processing method according to the present technology will be described with reference to FIG. 7. Note that FIG. 7 is a flowchart in the case of evaluating the device performance using eight types of light irradiation powers.

Figure 7:
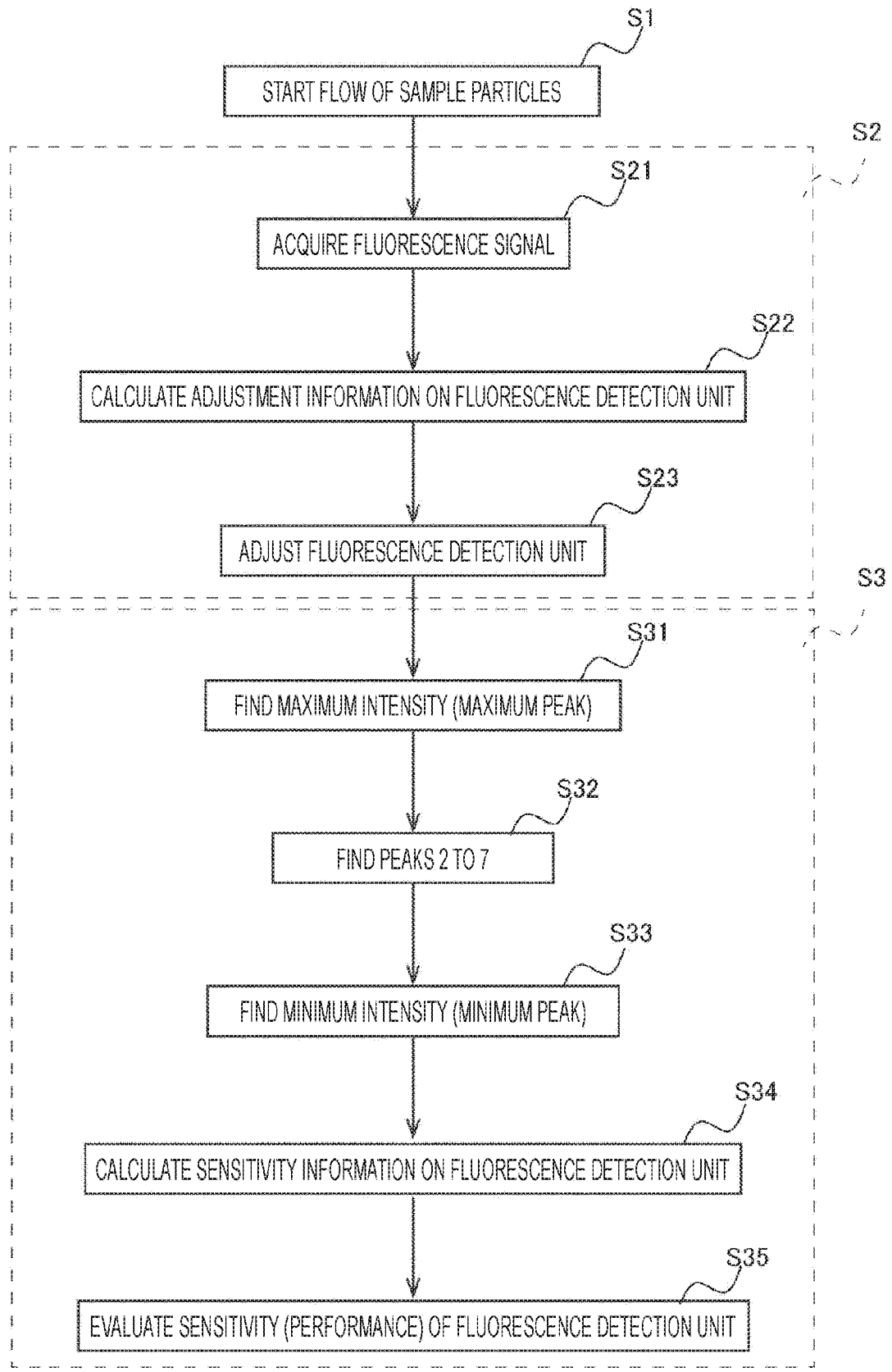
FIG. 7 is a flowchart illustrating a flow of an information process using an information processing method according to the present technology.

FIG. 7 is a flowchart illustrating a flow of the information process using the information processing method according to the present technology.

(1) Start Flow of Sample Particles (S1)

First, a sample including particles labeled with a fluorescent dye having a single fluorescence intensity (for example, align-check beads) is started to flow into the flow path.

(2) Device Adjustment (S2)

Next, the device is adjusted. The device is adjusted in the following procedure.

(2-1) Acquire Fluorescence Signal (S21) A fluorescence signal for adjusting the fluorescence detection unit is acquired from the sample.

(2-2) Calculate Adjustment Information on Fluorescence Detection Unit (S22)

The adjustment information on the fluorescence detection unit is calculated on the basis of the fluorescence signal obtained above.

(2-3) Adjust Fluorescence Detection Unit (S23)

For example, the adjustment of the fluorescence detection unit such as optical axis adjustment is performed on the basis of the adjustment information on the fluorescence detection unit calculated above.

(3) Device Performance Evaluation (S3) Next, the device performance is evaluated. In the present technology, the device performance can be evaluated as well, using the same particles as the sample particles used in the device adjustment (S2) described above. The device performance is evaluated in the following procedure.

(3-1) Find Maximum Intensity (Maximum Peak (Peak 8)) (S31)

First, the power of the excitation laser at a channel targeted for acquisition is set to a value at the time of normal measurement, and the channel and output level are set to reference values in order to activate a trigger with another laser. In this state, the sample including the particles labeled with the fluorescent dye having the single fluorescence intensity (for example, align-check beads) is released, and the output of the desired channel is adjusted with a high voltage (HV) of the fluorescence detection unit 13 (for example, photomultiplier tube (PMT)). Alternatively, a certain set HV value may be applied every time. In this state, a certain definite number of events is acquired.

(3-2) Find Peak 2 to Peak 7 (S32)

By altering only the power of the excitation laser at the channel targeted for acquisition, from the state in which data of the maximum intensity (maximum peak (peak 8)) was acquired, the sample including the particles labeled with the fluorescent dye having the single fluorescence intensity (for example, align-check beads) is released and a certain definite number of events is acquired. Each power is set under conditions that the histograms of the respective peaks do not overlap with each other and that the robust coefficient of variance (rCV) of a low output peak is large to some extent.

(3-3) Find Minimum Intensity (Minimum Peak (Peak 1)) (S33) The median value of the widths of the obtained seven pieces of peak data (data of the maximum peak and peak 2 to peak 7) is worked out, and the light irradiation power is set to a power at the time of measurement; then, data for only a sheath liquid, which does not contain the above data of the sample, is acquired at intervals of the worked-out median value of the widths.

(3-4) Calculate Sensitivity Information on Fluorescence Detection Unit (S34)

On the basis of the intensity range of each peak recognized through the steps from S1 to S3, information relating to the sensitivity of the fluorescence detection unit (the degree of linearity (Linearity), the fluorescence detection sensitivity (molecules of equivalent soluble fluorochromes (MESF), and the like), the Q value and the B value, and the like are calculated.

(3-5) Evaluate Sensitivity (Performance) of Fluorescence Detection Unit (S35)

The sensitivity (performance) of the fluorescence detection unit is evaluated on the basis of the sensitivity information on the fluorescence detection unit calculated above.

<Program>

In the present technology, the functions performed by the information processing unit 11 according to the present technology can also be stored as a program in a personal computer, or a hardware resource including a control unit including a central processing unit (CPU) and the like and a recording medium (such as a nonvolatile memory (a universal serial bus (USB) memory, and the like), a hard disk drive (HDD), or a compact disc (CD)), and the like, and caused to run by the personal computer or the control unit.

WORKING EXAMPLES

Hereinafter, the present technology will be described in more detail on the basis of working examples. Note that working examples described below indicate examples of representative working examples of the present technology, and the scope of the present technology is not narrowly interpreted by these working examples. In addition, the present working examples were carried out using "SP6800" manufactured by Sony Corporation.

First Experimental Example

In a first experimental example, using align-check beads as an example of a sample including particles labeled with a fluorescent dye having a single fluorescence intensity, data of eight peaks was acquired, and the sensitivity information on a BV421 channel was calculated.

[Method]

(1) A 488 nm laser was turned on at 40 mW, which is a power at the time of measurement, and a 405 nm laser was turned on at 60 mW, which is a power at the time of measurement.

(2) The forward scatter (FSC) at which a scattered signal by the 488 nm laser can be obtained was set as a trigger channel.

(3) The align-check beads were released, and the HV was adjusted such that the intensity of the BV421 channel fell within (Height Median)=$7\times10^5 \pm 7\times10^4$ (because the dynamic (D) range is $1\times10^6$).

(4) In this state, 2,500 events were acquired and taken as data of Peak 8.

(5) After setting the power of the 405 nm laser as indicated in Table 1 below, 2,500 events were acquired and taken as data of Peak 2 to Peak 7.

(6) The median value of the widths of Peak 2 to Peak 8 was calculated.

(7) The 405 nm laser was set to 60 mW, which is a power at the time of measurement.

(8) Beads were not released, but only a sheath liquid was released, and an auto-trigger was activated; then 2,500 events were measured with the width of (6) and taken as data of Peak 1.

(9) Pre-computed molecules of equivalent fluorochromes (MEF) were used for Peak 8, and MEF based on the power ratio of Peak 8 were worked out for Peak 2 to Peak 7.

(10) An MEF-Data regression line was obtained from the MEF and the median value of areas of Peak 2 to Peak 8.

(11) The degree of linearity (Linearity), the fluorescence detection sensitivity (MESF), the Q value, and the B value were calculated.

TABLE 1

| | BV421 405 nm Laser |
|---|---|
| Peak 8 | 60.0 mW |
| Peak 7 | 40.1 mW |
| Peak 6 | 20.2 mW |

TABLE 1-continued

| | BV421 405 nm Laser |
|---|---|
| Peak 5 | 10.3 mW |
| Peak 4 | 5.3 mW |
| Peak 3 | 2.5 mW |
| Peak 2 | 1.0 mW |

[Result]
The result is illustrated in FIG. 2.

Second Experimental Example

In a second experimental example, using align-check beads as an example of a sample including particles labeled with a fluorescent dye having a single fluorescence intensity, data of eight peaks was acquired, and the sensitivity information on a PE channel was calculated.

[Method]
(1) A 488 nm laser was turned on at a measurement power of 40 mW, and a 638 nm laser was turned on at 60 mW, which is a power at the time of measurement.
(2) An APC channel at which high level fluorescence can be obtained by the 638 nm laser was set as a trigger.
(3) The align-check beads were released, and the HV was adjusted such that the intensity of the PE channel fell within (Height Median)=$7\times10^5\pm7\times10^4$ (because the D range is $1\times10^6$).
(4) In this state, 2,500 events were acquired and taken as data of Peak 8.
(5) After setting the 488 nm laser as indicated in Table 2 below, 2,500 events were acquired and taken as data of Peak 2 to Peak 7.
(6) The median value of the widths of Peak 2 to Peak 8 was calculated.
(7) The 488 nm laser was set to 60 mW, which is a power at the time of measurement.
(8) Beads were not released, but only a sheath liquid was released, and an auto-trigger was activated; then 2,500 events were measured with the width of (6) and taken as data of Peak 1.
(9) Pre-computed MEF were used for Peak 8, and MEF based on the power ratio of Peak 8 were worked out for Peak 2 to Peak 7.
(10) An MEF-Data regression line was obtained from the MEF and the median value of areas of Peak 2 to Peak 8.
(11) The degree of linearity (Linearity), the fluorescence detection sensitivity (MESF), the Q value, and the B value were calculated.

TABLE 2

| | PE 488 nm Laser |
|---|---|
| Peak 8 | 40.0 mW |
| Peak 7 | 24.6 mW |
| Peak 6 | 14.6 mW |
| Peak 5 | 8.6 mW |
| Peak 4 | 3.8 mW |
| Peak 3 | 1.8 mW |
| Peak 2 | 0.8 mW |

[Result]
The result is illustrated in FIG. 3.
Note that the present technology can also have the following configurations.
(1)
An information processing device including an information processing unit that acquires a plurality of fluorescence intensities at a plurality of light irradiation powers for a fluorescence signal from a sample including particles labeled with a fluorescent dye having a single fluorescence intensity, recognizes an intensity range of each of the plurality of fluorescence intensities detected on the basis of a fluorescence intensity balance of the sample, and calculates information relating to sensitivity of a fluorescence detection unit.
(2)
The information processing device according to (1), in which the light irradiation powers include at least three or more different powers.
(3)
The information processing device according to (2), in which the light irradiation powers include at least five or more different powers.
(4)
The information processing device according to (1), in which the information processing unit recognizes a fluorescence intensity range obtained from a sheath liquid that does not contain the sample, as a minimum intensity range, and calculates the information relating to the sensitivity of the fluorescence detection unit.
(5)
The information processing device according to (1), in which the information relating to the sensitivity of the fluorescence detection unit includes a degree of linearity between the fluorescence intensities and a number of particles and/or fluorescence detection sensitivity.
(6)
The information processing device according to (1), in which a trigger is activated at a constant light irradiation power by an excitation laser different from an excitation laser for acquiring the plurality of fluorescence intensities at the plurality of light irradiation powers.
(7)
The information processing device according to (1), in which the information processing unit also calculates information relating to adjustment of the fluorescence detection unit on the basis of the fluorescence signal from the sample including the particles labeled with the fluorescent dye having the single fluorescence intensity.
(8)
An information processing system including:
an irradiation unit that irradiates a sample including particles labeled with a fluorescent dye having a single fluorescence intensity with light;
a detection unit that detects a fluorescence signal from the sample; and
an information processing unit that acquires a plurality of fluorescence intensities at a plurality of light irradiation powers for the fluorescence signal, recognizes an intensity range of each of the plurality of fluorescence intensities detected on the basis of a fluorescence intensity balance of the sample, and calculates information relating to sensitivity of the detection unit.
(9)
An information processing method that performs an information processing step of acquiring a plurality of fluorescence intensities at a plurality of light irradiation powers for a fluorescence signal from a sample including particles labeled with a fluorescent dye having a single fluorescence intensity, recognizing an intensity range of each of the plurality of fluorescence intensities detected on the basis of a fluorescence intensity balance of the sample, and calculating information relating to sensitivity of a fluorescence detection unit.

REFERENCE SIGNS LIST

1 Information processing device
11 Information processing unit
10 Information processing system
12 Light irradiation unit
13 Fluorescence detection unit
14 Sorting unit

The invention claimed is:

1. An information processing device, comprising:
at least one processor configured to:
acquire a plurality of fluorescence intensities at a plurality of light irradiation powers for a fluorescence signal from a sample, wherein the sample includes a plurality of particles labeled with a fluorescent dye having a single fluorescence intensity;
recognize an intensity range of each fluorescence intensity of the plurality of fluorescence intensities based on fluorescence intensity balance of the sample; and
calculate information related to a sensitivity of a photodetector based on the intensity range.

2. The information processing device according to claim 1, wherein the plurality of light irradiation powers includes at least three or more different powers.

3. The information processing device according to claim 1, wherein the plurality of light irradiation powers includes at least five or more different powers.

4. The information processing device according to claim 1, wherein the at least one processor is further configured to:
recognize a fluorescence intensity range, obtained from a sheath liquid that does not contain the sample, as a minimum intensity range; and
calculate the information related to the sensitivity of the photodetector.

5. The information processing device according to claim 1, wherein
the information related to the sensitivity of the photodetector includes at least one of a degree of linearity between the plurality of fluorescence intensities and a number of the plurality of particles or a fluorescence detection sensitivity, and
the fluorescence detection sensitivity corresponds to molecules of equivalent soluble fluorochromes (MESF).

6. The information processing device according to claim 1, wherein a trigger is activated at a constant light irradiation power by a first excitation laser different from a second excitation laser used to acquire the plurality of fluorescence intensities at the plurality of light irradiation powers.

7. The information processing device according to claim 1, wherein the at least one processor is further configured to calculate information related to adjustment of the photodetector based on the fluorescence signal from the sample including the plurality of particles labeled with the fluorescent dye having the single fluorescence intensity.

8. The information processing device according to claim 1, wherein the at least one processor is further configured to acquire a background signal of the photodetector based on a light irradiation power of the plurality of light irradiation powers that causes fewest fluorescence peaks.

9. An information processing system, comprising:
a laser configured to irradiate a sample which includes a plurality of particles labeled with a fluorescent dye having a single fluorescence intensity with light;
a photodetector configured to detect a fluorescence signal from the sample; and
at least one processor configured to:
acquire a plurality of fluorescence intensities at a plurality of light irradiation powers for the fluorescence signal;
recognize an intensity range of each fluorescence intensity of the plurality of fluorescence intensities based on fluorescence intensity balance of the sample; and
calculate information related to a sensitivity of the photodetector based on the intensity range.

10. An information processing method, comprising:
acquiring a plurality of fluorescence intensities at a plurality of light irradiation powers for a fluorescence signal from a sample, wherein the sample includes a plurality of particles labeled with a fluorescent dye having a single fluorescence intensity;
recognizing an intensity range of each fluorescence intensity of the plurality of fluorescence intensities based on a fluorescence intensity balance of the sample; and
calculating information related to a sensitivity of a fluorescence detection unit based on the intensity range.

* * * * *